United States Patent [19]

Schefczik

[11] Patent Number: 4,611,064
[45] Date of Patent: Sep. 9, 1986

[54] PREPARATION OF INDOLE DERIVATIVES

[75] Inventor: Ernst Schefczik, Ludwigshafen, Fed. Rep. of Germany

[73] Assignee: BASF Aktiengesellschaft, Rheinland, Fed. Rep. of Germany

[21] Appl. No.: 788,575

[22] Filed: Oct. 17, 1985

[30] Foreign Application Priority Data

Oct. 18, 1984 [DE] Fed. Rep. of Germany ....... 3438218

[51] Int. Cl.$^4$ .................. C07D 209/36; C07D 209/42
[52] U.S. Cl. ........................................ 548/484; 544/94
[58] Field of Search ........................... 548/484; 544/94

[56] References Cited

U.S. PATENT DOCUMENTS 3,238,201  3/1966  Scherrer ............................... 544/94

FOREIGN PATENT DOCUMENTS 111890  6/1900  Fed. Rep. of Germany .

OTHER PUBLICATIONS

Chemical Abstracts, vol. 102, 185098d and DD A1 213435.
Chemical Abstracts, vol. 84, 105518n & J. Org. Chem. 41, 825/31.
Chemical Abstracts, vol. 83, 147436u and J. Het. Chem., 12, 565/72.

Primary Examiner—Richard L. Raymond
Attorney, Agent, or Firm—Oblon, Fisher, Spivak, McClelland & Maier

[57] ABSTRACT

Compounds which, in one of the possible tautomeric forms and as free acidic compounds, are of the general formula I

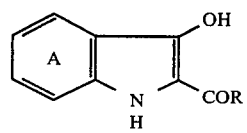

where R is unsubstituted or substituted alkyl, alkoxy, cycloalkoxy or aryloxy and the ring A may be further substituted, are prepared by a process in which a compound of the formula II

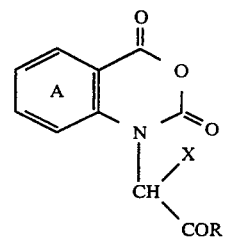

where X is hydrogen or an alkoxycarbonyl group and R has the above meanings with the exception of unsubstituted or substituted alkyl, is converted in an alcoholate-containing solution, and the product is then acidified.

The compounds prepared according to the invention are useful intermediates for the preparation of dyes.

3 Claims, No Drawings

PREPARATION OF INDOLE DERIVATIVES

The present invention relates to the preparation of indole derivatives. According to the invention there is provided a process for the preparation of a compound which, in one of the possible tautomeric forms and as a free acidic compound, is of the general formula I

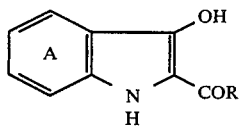

where R is unsubstituted or substituted alkyl, alkoxy, cycloalkoxy or aryloxy, and the ring A may be further substituted, wherein a compound of the formula II

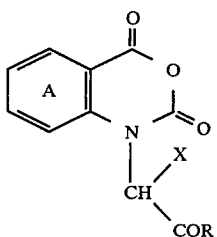

where X is hydrogen or an alkoxycarbonyl group and R has the above meaning with the exception of unsubstituted or substituted alkyl, is converted in an alcoholate-containing solution and the product then acidified.

R suitably contains up to 8 carbon atoms and may, for example, be $CH_3$, $C_2H_5$, $C_3H_7$, $C_7H_9$, $OCH_3$, $OC_2H_5$, $OC_3H_7$, $OC_4H_9$, $OC_6H_{13}$, $OC_8H_{17}$, $OCH_2C_6H_5$, $OC_6H_5$, $OC_6H_5Cl$, $OC_6H_5CH_3$, $OC_2H_4OCH_3$, $OC_2H_4OC_2H_5$, $OC_2H_4OC_4OC_4H_9$ or

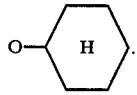

The ring A may be further substituted by, for example, fluorine, chlorine, bromine, $CH_3$, $C_2H_5$, $OCH_3$, $OC_2H_5$ or $OC_4H_9$.

The compounds of the formula II are advantageously converted in an alcoholate-containing alcoholic solution, for example in methanol, ethanol, propanol or butanol, these solvents containing the corresponding alcoholate, e.g. the sodium or potassium alcoholate, in an amount of about 5-50% by weight. Not less than 1 mole of alcoholate, but preferably an excess, e.g. from 2 to 3 moles, should be used per mole of the compound of the formula II.

Other solvents, such as dimethylformamide, N-methylpyrrolidone or dimethyl sulfoxioe, may be present but are not necessary. The reaction can be carried out even at low temperatures, e.g. from 0° to 20° C.; if higher reaction rates are desired, the mixture may of course be heated.

The products initially obtained are the indoxyl salts, and the cation is derived from the alcoholate, i.e. is, as a rule, Na⊕ or K⊕. The compounds of the formula I are then obtained by acidification, for example with hydrochloric acid, sulfuric acid or acetic acid.

Some of the compounds of the formula I are known, and can be used as dye intermediates.

The novel process is particularly important for the preparation of compounds of the formula I in which R is $OCH_3$ or $OC_2H_5$ and the ring A is unsubstituted or carries a 4-halogen atom.

The compounds of the formula II are novel and can be prepared by alkylation of isatoic anhydride e.g. as described in the following examples.

In the Examples which follow, parts and percentages are by weight, unless stated otherwise.

EXAMPLE 1

(a) 115 parts of methyl monochloroacetate and 163 parts of isatoic anhydride are introduced into 200 parts by volume of dimethylformamide, and the mixture is stirred at 60° C. 110 parts of triethylamine are then added dropwise, and stirring is continued for 4 hours at 60° C. Triethylamine hydrochloride begins to crystallize out. The mixture is stirred into 2000 parts of ice/water, and the precipitated product is filtered off under suction, washed with water and dried to give 231 parts of N-methoxycarbonylmethyleneisatoic anhydride. A sample recrystallized from acetic acid had a melting point of 179°–180° C. and gave the following analytical data:

$C_{11}H_9NO_5$ (235). Calculated: C, 56.2; H, 3.9; N, 6.0; 0, 34.0. Found: C, 56.4; H, 4.0; N, 6.0; 0, 33.9.

The same compound is obtained if anhydrous sodium carbonate or sodium bicarbonate is useo instead of the triethylamine.

(b) 235 parts of N-methoxycarbonylmethyleneisatoic anhydride are introduced into 600 parts of a 20% strength solution of sodium methylate in methanol. The mixture is refluxed for 2 hours and left to cool, after which it is diluted with an equal volume of ice water and acidified with hydrochloric acid. The precipitated product is filtered off under suction, washed with water and dried to give 170 parts of methyl indox-2-ylcarboxylate of melting point 147°–148° C. (from toluene). Annlysis gave the following results:

$C_{10}H_9NO_3$ (191). Calculated: C, 62.8; H, 4.7; N, 7.3; 0, 25.1 Found: C, 62.6; H, 4.9; N, 7.3; 0, 25.1.

EXAMPLE 2

(a) If the methyl monochloroacetate of Example 1 a) is replaced with 130 parts of ethyl monochloroacetate and the procedure is otherWise carried out as described in Example 1 (a), 229 parts of N-ethoxycarbonylmethyleneisatoic anhydride of melting point 144°–145° C. (from ethanol) are obtained.

(b) 249 parts of N-ethoxycarbonylmethyleneisatoic anhydride are introduced a little at a time into a sodium ethylate solution prepared by dissolving 65 parts of metallic sodium in 800 parts by volume of absolute ethanol. During the addition, the temperature increases, and the reaction mixture is kept at 30°–40° C. by cooling. When the exothermic reaction has died down, crystals begin to separate out. Stirring is continued for 8 hours at room temperature, and the mixture is poured onto 1000 parts of ice water and acidified with sulfuric acid. The product is filtered off under suction, washed with water and dried to give 173 parts of ethyl indox-2-yl-carboxylate of melting point 117°–118° C. (from toluene/ cyclohexane). The compound is identical to a sample prepared as described by Vorländer, B.35, 1694.

EXAMPLE 3

(a) 240 parts of diethyl bromomalonate and 163 parts of isatoic anhydride are introduced into 250 parts by volume of N-methylpyrrolidone, and the mixture is stirred at 60° C. Thereafter, 120 parts of triethylamine are added dropwise, ano stirring is continued for 12 hours at 60°–70° C. When precipitation is effected by pouring the mixture onto ice water, the product separates out initially in semisolid form and crystallizes completely on standing overnight. It is comminuted, filtered off under suction, washed with water and dried to give 300 parts of the compound of the constitution

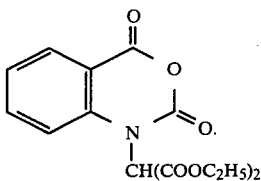

When this compound is recrystallized from toluene, the product obtained melts at 117°–118° C. Analysis gives the following results:

$C_{15}H_{15}NO_7$ (321) Calculated: C, 56.1; H, 4.7; N, 4.4; 0, 34.9. Found: C, 56.0; H, 4.8; N, 4.4; 0, 34.6.

(b) 150 parts of sodium methylate are dissolved in 2000 parts by volume of absolute ethanol, after which 321 parts of the compound obtained as described in 3 (a) are introduced. The compound dissolves and, when the addition is complete, crystals separate out. The reaction mixture is stirred for 6 hours at 30°–40° C. and poured onto 2000 parts of ice water, a clear solution being obtained. Hydrochloric acid at pH2 is added, the product being precipitated in crystalline form. It is filtered off under suction, washed with water and dried to give 159 parts of ethyl indox-2-ylcarboxylate, which is identical to the compound prepared as described in 2(b).

EXAMPLE 4

110 parts of methyl monochloroacetate and 163 parts of isatoic anhydride are introduced into 180 parts by volume of N-methylpyrrolidone. 105 parts of triethylamine are added dropwise to the mixture at 60° C., and stirring is continued for 6 hours at this temperature. A solution of 180 parts of sooium methylate in 500 parts by volume of methanol is then run in at a rate such that the temperature of the reaction mixture remains at 60° C. without heating. Stirring is continued for 4 hours at 60° C., and the mixture is poured onto 1000 parts of ice water and excess hydrochloric acid. The solid product precipitated is filtered off unoer suction, washed with water and dried to give 156 parts of methyl indoxylcarboxylate, which is identical to the compound obtained as described in Example 1 (b).

EXAMPLE 5

The procedure described in Example 4 is followed, except that the monochloroacetate is replaced with 140 parts of bromoacetone. When the mixture is worked up, 139 parts of indox-2-yl methyl ketone of melting point 134°–135° C. (from dilute ethanol) are obtained. The compound obtained is identical to a sample prepared as described in German Pat. No. 111,890.

EXAMPLE 6

(a) 197.5 parts of 6-chloroisatoic anhydride are added to a mixture of 300 parts by volume of dimethylformamide and 115 parts of methyl monochloroacetate which is stirred at 60° C., after which 110 parts of triethylamine are added dropwise in the course of 30 minutes. Stirring is continued for 6 hours at 60° C., and the mixture is then diluted with 2500 parts of water and cooled. The product is filtered off under suction, washed with water and dried to give 247 parts of N-methoxycarbonylmethylene-6-chloroisatoic anhydride of melting point 167°–168° C. (from acetic acid). Calculated: Cl 13.2, found: Cl 13.4%.

(b) 125 parts of sodium methylate are dissolved in 900 parts by volume of methanol. 269.5 parts of the compound obtained as described in Example 6(a) are added to the solution, and the mixture is stirred for 12 hours at 40° C. 1200 parts of water are added to the suspension of crystals, a clear solution being formed. The solution is acidified with sulfuric acid, and the precipitated product is filtered off under suction, washed with water and dried to give 199 parts of the compound

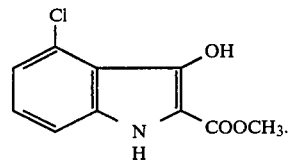

A sample recrystallized from toluene has a melting point of 160°–161° C. and contains 15.8% of Cl (calculated: 5.7%).

EXAMPLE 7

(a) If the methyl monochloroacetate in Example 6 (a) is replaced with 130 parts of ethyl monochloroacetate and the procedure is otherwise carried out as described in Example 6 (a), 254 parts of N-ethoxycarbonylmethylene-6-chloroisatoic anhydride of melting point 180°–181° C. (from acetic acid) are obtained. The chlorine content is found to oe 12.9% (calculated: 12.5%).

(b) 150 parts of sodium methylate are dissolved in 1500 parts by volume of absolute ethanol, ano 283.5 parts of the compound obtained as described in Example 6(a) are then introduced. Soon after the end of the addition, crystallization begins in the clear solution. The crystal slurry is stirred for 6 hours at 55° C. and dissolved in 2000 parts of water, and the solution is acidified with hydrochloric acid, ethyl 4-chloroindox-2-ylcarboxylate being precipitated. This product is filtered off under suction, washed with water and dried. Yield: 189 parts; melting point: 152°–153° C. (from toluene); chlorine content: 15.1% (calculated 14.8%).

EXAMPLE 8

(a) 120 parts of methyl monochloroacetate and 242 parts of 5-bromoisatoic anhydride are introduced into 300 parts by volume of N-methylpyrrolidone. 110 parts of triethylamine are added dropwise to the solution at 60° C., and stirring is continued for a further 6 hours at this temperature. Thereafter, precipitation is effected by pouring the mixture onto 2000 parts of water, and the product is filtered off under suction, washed with water and dried to give 302 parts of N-methoxycarbonylmethylene-5-bromoisatoic anhydride having a melting point of 210°–211° C. (from acetic acid) and a bromine content of 25.8% (calculated 25.4%).

(b) 180 parts of sodium methylate are dissolved in 1800 parts by volume of methanol. 314 parts of the compound obtained as described in Example 8 a) are added to this solution. The reaction mixture is stirred for 12 hours at 40° C., 2000 parts of water are added and the mixture is acidified with hydrochloric acid, methyl 5-bromoindox-2-ylcarboxylate being precipitated. The product is filtered off under suction, washed with water and dried. Yield: 228 parts; melting point: 196°–197° C. (from glacial acetic acid); bromine content: 29.2% (calculated 29.6%).

I claim:

1. A process for the preparation of a compound which, in one of the possible tautomeric forms and as a free acidic compouno, is of the formula I

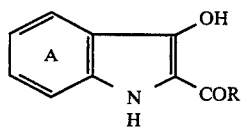

where R is unsubstituted or substituted alkyl, alkoxy, cycloalkoxy or aryloxy, and the ring A may be further substituted, wherein a compound of the formula II

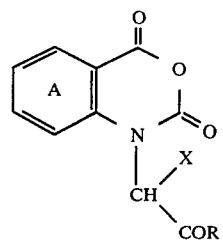

where X is hydrogen or an alkoxycarbonyl group and R has the above meanings with the exception of unsubstituted or substituted alkyl, is converted in an alcoholate-containing solution and the product then acidified.

2. A process as claimed in claim 1, wherein a compound of formula II is used in which R is $OCH_3$ or $OC_2H_5$ and the ring A is unsubstituted or carries a 4-halogen atom.

3. A process as claimed in claim 1 or 2, wherein the conversion is carried out in a solution in methanol, ethanol, propanol or butanol containing the corresponding sodium or potassium alcoholate in an amount of 5 to 50% by weight.

* * * * *